United States Patent [19]

Kingsbury

[11] 4,085,100
[45] Apr. 18, 1978

[54] INTERMEDIATE FOR DEPHTHALOYLATION OF AZETIDINONE COMPOUNDS

[75] Inventor: William D. Kingsbury, King of Prussia, Pa.

[73] Assignee: SmithKline Corporation, Philadelphia, Pa.

[21] Appl. No.: 737,297

[22] Filed: Nov. 1, 1976

[51] Int. Cl.$^2$ .................. A61K 31/395; C07D 205/06
[52] U.S. Cl. ........................ 260/239 A; 260/250 AC; 260/326 N; 424/244
[58] Field of Search .................................... 260/239 A

[56] References Cited

U.S. PATENT DOCUMENTS

| 3,703,512 | 11/1972 | Hausler et al. | 260/239 A |
| 3,816,408 | 6/1974 | Gladych et al. | 260/239 A |
| 3,832,347 | 8/1974 | Kukolja et al. | 260/239 A |

OTHER PUBLICATIONS

Kukolja et al., "J. Am. Chem. Soc.," vol. 97, 1975, pp. 5582–5583.

Primary Examiner—Donald G. Daus
Assistant Examiner—James H. Turnipseed
Attorney, Agent, or Firm—William H. Edgerton

[57] ABSTRACT

A method for dephthaloylation of azetidinone compounds which contain a phthalimido group to produce useful aminoazetidinone intermediates comprises reaction with methyl hydrazine at low temperatures.

5 Claims, No Drawings

INTERMEDIATE FOR DEPHTHALOYLATION OF AZETIDINONE COMPOUNDS

This invention comprises an improved method for removing the protective phthaloyl group from amine functions on azetidinone containing compounds characterized by using methyl hydrazine with temperature control. This invention also includes intermediates formed in the method which are characterized by being a phthaloyl $N^1$-methylhydrazide. These are referred to herein as either open or half hydrazides.

Azetidinone containing compounds are well known to have various antibacterial activities particularly among compounds which have bicyclic systems in their structures as do the penicillin or cephalosporin compounds. The intact azetidinone ring is commonly accepted in the art to be essential to the activity of the end products. Splitting of the lactam ring is a common side reaction of unsuccessful synthetic procedures which generally give inactive open chain compounds.

Also a large number of monocyclic azetidinones are described in the literature to be either useful as intermediates for preparing bicyclic antibacterial agents or as end products having antibacterial activity in themselves. For example, Belgium Ser. No. 0/166,530 demonstrates the utility of the free 3-amino-4-oxoazetidines used to illustrate this invention as well as the preparation of certain phthalimido starting materials.

The prior art has described various methods for dephthaloylation of azetidinone intermediates using hydrazine, methylamine, dimethylaminopropylamine, etc. See for example S. Wolfe et al., Can. J. of Chem. 48, 3572 (1970) or the presentation on the monocyclic antibacterial, nocardicin, Symposium on Recent Advances in the Chemistry of β-Lactam Antibiotics, Cambridge, U.K. June 28-30, 1976. The difficulties of the prior art due to the fact that "the azetidinone carbonyl function is, in fact, more sensitive toward hydrazine than the phthalimido carbonyl" are summed up by S. Kukolja et al., J. Am. Chem. Soc. 97, 5582 (1975). Kukolja has reported that hydrazine and methylhydrazine will split a phthalisoimide derivative but this is a process remote from that claimed herein.

I have now unexpectedly found that methylhydrazine easily forms a $N^1$-methylphthaloylhydrazide intermediate with phthalimidoazetidinones at low temperatures and that these intermediates split spontaneously at higher temperatures to give the desired aminoazetidinones in good yield, for example from 75-90% overall.

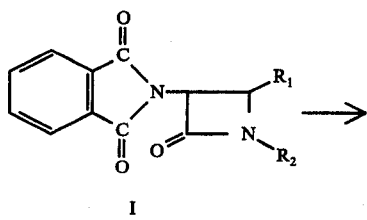

I

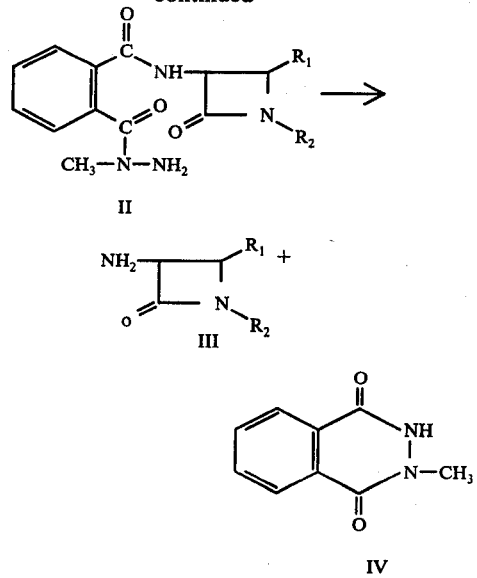

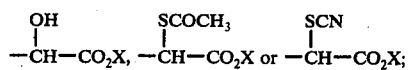

$R_1$ and $R_2$ in the above noted structure, either separately or when combined into a bicyclic azetidinone structure, should not include any centers reactive to methylhydrazine under the conditions of this reaction as will be evident to one skilled in the art.

In fact the improvement of this invention has given best results in the monolactam series in which $R_1$ is —COOY or —CH$_2$OZ and $R_2$ is 2,4-dimethoxybenzyl (DMB), benzhydryl (BH), trityl, hydrogen or glycolic or thioglycolic esters such as $$\underset{-\text{CH}-\text{CO}_2\text{X},}{\overset{\text{OH}}{|}} \quad \underset{-\text{CH}-\text{CO}_2\text{X or}}{\overset{\text{SCOCH}_3}{|}} \quad \underset{-\text{CH}-\text{CO}_2\text{X};}{\overset{\text{SCN}}{|}}$$

Y is lower alkyl of 1-6 carbon atoms, benzyl, methoxybenzyl, halobenzyl, phenyl, or 2,2,2-trichloroethyl; Z is lower alkyl of 1-6 carbons, lower alkanoyl of 2-6 carbon atoms, mesyl (CH$_3$SO$_2$—), tosyl (p-tolylSO$_2$—) or benzyl and X is an easily removable carboxy protective group such as benzhydryl, 2,2,2-trichloroethyl, p-nitrobenzyl and the like as disclosed in "Protective Groups in Organic Chemistry" J. F. W. McOmie, Plenum, 1973.

The compounds are preferably cis at the 2,3-positions of the azetidinone ring. The intermediate compounds of Structure II with $R_1$ and $R_2$ as described above which are open or half hydrazides are believed to be novel intermediates and as such are an important part of this invention. The open hydrazide intermediates (II) are unstable to heat or extended standing at room temperature even in the dry form. To isolate the intermediate in more stable form it is possible to N-acylate the hydrazide such as with acetic anhydride or trifluoroacetic anhydride in methylene chloride solution. Alternatively the reaction mixture per se can be reacted with an acylating agent to form the N-acyl derivative. Of course a wide range of acylating agents may be so used.

The starting materials of Structure I are prepared as described in the Belgian patent referred to above. The compounds in which $R_2$ is a glycolate-like ester are prepared by reacting the compound in which $R_2$ is hydrogen with butyl lithium to form the N-lithium compound which then is reacted with a glyoxalate ester to form the desired compound.

The reaction of this invention is carried out by dissolving the phthalimido containing azetidinone starting material (I) in an inert organic solvent in which the reactants are soluble at the temperature of the reaction, that is, in the cooled state. The temperature may vary from about −80° to 0° preferably from about −80° to −25°. Most conveniently the reaction is run at ambient temperature in a dry ice-solvent bath. The methylhydrazine in stoichiometric amounts or preferably in excess is added to the cooled reaction mixture. Reaction begins almost at once. Progress is measured by thin layer chromatography, for example using silica gel with 10% ethyl acetate/chloroform. If the reaction does not seem complete in a reasonably short time the reaction temperature is allowed to warm up carefully toward room temperature with monitoring of the progress of the reaction with optional addition of more methylhydrazide. The intermediate phthaloyl-$N^1$-methylhydrazide (II) is optionally isolated by evaporating the solvent in vacuo without heating. It may be purified by methods known to the art.

The intermediate hydrazide preferably without isolation is warmed at temperatures from about room temperature (about 25°–30°) to the boiling point of the reaction mixture or moderate steam bath temperature (40°–75° C.) to split off the phthaloylhydrazide. When the reaction solvent is the preferred methylene chloride or chloroform the reaction can usually be monitored by the appearance of a granular solid which is the by-product, methylphthaloylhydrazide (IV). The reaction temperature therefore ranges from about 25°–75° preferably about 30°–50°. The time of reaction varies from overnight at room temperature (10 hours) to about ½–3 hours at 75°.

The solvent for the overall reaction can vary widely but is preferably a halogenated hydrocarbon solvent such as chloroform, carbon tetrachloride, methylene chloride, alcoholic solvents such as ethanol or methanol, an ethereal solvent such as tetrahydrofuran or an amide solvent such as dimethylacetamide or dimethylformamide.

The general utility of this invention as a synthetic tool for the synthetic antibiotic chemist is obvious. The Kukolja publication attests to this. The antibacterial end products which are made from 3-aminoazetidinones such as those made using this invention have well known acylamino groups such as the 7-acylamino groups known to the cephalosporin art or the 6-acylamino groups known to the penicillin art. Certain specific such moieties are the D-phenylglycylamino 7-substituents such as those in the structures of ampicillin or cephalexin or the mandelylamino substituents such as that in cefamandole. The N-acylated compounds having antibiotic activity are prepared by known prior art methods.

The unexpected nature of the claimed invention is also evident because it can be run on phthalimido azetidinones having substituents which might be normally expected to be sensitive to a hydrazine such as a carboxylic ester, a mesylate or tosylate, etc. In the presence of such sensitive functions the reaction is run at as low a temperature as possible with appropriate t.l.c. monitoring. Of course one skilled in the art will recognize certain groups which should not be present on the phthalimidoazetidinone such as strong acid groups unless reaction at these centers is also desired by the operator.

The following examples are designed to demonstrate the operation of this invention but not to limit its scope. All temperatures are on the Centigrade scale.

EXAMPLE 1

2,4-Dimethoxybenzylamine (5.01 g, 0.03 mol) and methyl glyoxolate (3.17 g, 0.036 mol) are condensed in the presence of anhydrous magnesium sulfate in 150 ml of methylene chloride at 0°–5° for 2 hours. The resulting imine is dissolved in methylene chloride (800 ml) and cooled in an ice bath. Triethylamine (5.4 ml) is added followed by the dropwise addition of a solution of N-phthalimido acetic acid chloride (7.54 g, 0.0338 mol) [J. Amer. Chem. Soc., 71, 1856 (1949)] in methylene chloride (80 ml). After the reaction is stirred 2 hours, the solution is concentrated and then is washed with water, dilute hydrochloric acid, and dilute sodium bicarbonate. The dried organic phase is evaporated to give methyl cis-1-(2,4-dimethoxybenzyl)-3-phthalimido-4-oxoazetidine-2-carboxylate which is triturated with ether; 6.4 g (50%).

The lactam product from above (8.0 g) was dissolved in 80 ml of methylene chloride and cooled in a dry ice-acetone bath under nitrogen then 1.1 g of methylhydrazine was added. After stirring for 20 minutes the volatiles were removed at the pump to give 8.3 g of the open hydrazide intermediate (II, $R_1 = -CO_2CH_3$; $R_2$ is DMB). This solid compound (3.5 g) in 50 ml of chloroform was heated on the steam bath for 30 minutes then allowed to stand overnight. Solid IV was separated by filtration and the supernatent liquid was evaporated to give a yellow oil of mostly cis-3-amino compound which may be optionally purified over a silica gel column using chloroform:isopropanol. Trituration of the oil under petroleum ether produced a solid.

The yellow oil in 25 ml of methylene chloride cooled to 0° was reacted with 1.3 g of phenoxyacetyl chloride and 1 ml of triethylamine to give the 3-phenoxyacetamido derivative, m.p. 114.5°–115.5°.

EXAMPLE 2

To a mixture containing 4.16 g (22.7 mmole) of benzhydrylamine and anhydrous magnesium sulfate in 50 ml of dichloromethane at 25° was added a solution of 2.96 g (22.7 mmole) of n-butyl glyoxylate in 50 ml of dichloromethane. The reaction mixture was stirred at room temperature overnight and then was filtered and the solvents were removed in vacuo to afford the imine intermediate.

This compound (0.03 mol) is reacted with a slight excess of N-phthalimidoacetyl chloride in the presence of triethylamine in methylene chloride as in Example 2 to give butyl cis-1-benzhydryl-3-phthalimido-4-oxo-2-azetidine-carboxylate which (0.005 mol) is then reacted with an excess of methylhydrazine (0.006 mol) in methylene chloride at −75° to −80° to give the half hydrazide which is isolated by evaporating of the volatiles in vacuo (II, $R_1 = -CO_2C_4H_9$; $R_2 = BH$). The reaction mixture is alternatively then heated on the steam bath for 2 hours, filtered and the reaction liquor separated. Evaporation of the washed organic extracts gives n-butyl cis-1-benzhydryl-3-amino-4-oxo-2-azetidinecarboxylate.

EXAMPLE 3

A mixture of 250 mg of butyl cis-1-benzhydryl-3-phthalimido-4-oxo-2-azetidine carboxylate, 473 mg (1.75 mmole) of potassium persulfate, 307 mg (0.858 mmole) of disodium phosphate dodecahydrate, 9.2 ml of water and 8.4 ml of acetonitrile is thoroughly degassed with argon and then heated to 80°–85° under argon for three hours. The reaction mixture is cooled and the acetonitrile removed on the rotary evaporator. The aqueous residue is saturated with solid sodium chloride and extracted three times with ethyl acetate. The combined organic extractions are washed with brine, dried over anhydrous sodium sulfate, filtered, and concentrated in vacuo to give crude butyl cis-3-phthalimido-4-oxo-2-azetidinecarboxylate.

This material (100 mg.) in chloroform at dry ice-acetone temperature is reacted with an excess of methylhydrazine with warming to room temperature. A portion of the reaction mixture is evaporated in vacuo overnight to give the half hydrazide (II, $R_1 = -CO_2C_4H_9$; $R_2 = H$). The remaining reaction mixture is heated at 35° for 3 hours to give butyl cis-3-amino-4-oxo-2-azetidine carboxylate.

The reaction may be carried out similarly using the methylcarboxylate.

EXAMPLE 4

Various methoxy substituted benzyl or polyphenylmethylamines can be substituted in the reactions of Examples 1–3 such as 4-methoxybenzhydrylamine, 4,4'-dimethoxybenzhydrylamine, 2,3-dimethoxybenzhydrylamine, 2,2', 4,4'-tetramethoxybenzhydrylamine, tritylamine, 4-methoxybenzylamine or 4-nitrobenzylamine. Also equimolar quantities of other glyoxalates may be used such as benzyl glyoxalate, isoamyl glyoxalate, hexyl glyoxalate, trichloroethyl glyoxalate or p-methoxybenzyl glyoxalate.

These give the corresponding half hydrazide, alkyl 3-amino-4-oxo-2-azetidine carboxylate or the N-benzyl or polyphenylmethyl congeners. All of these are intermediates and can be converted to active mono or bicyclo antibacterial products as described and as known to the art.

EXAMPLE 5

A solution of 8.0 g of methyl cis-1-(2,4-dimethoxybenzyl)-3-phthalimido-4-oxoazetidine-2-carboxylate in methylene chloride was cooled in a dry ice-acetone bath under nitrogen. Methylhydrazine (98%, 1.1 g) was added in one portion. The reaction mixture turned yellow. After stirring for 20 minutes, the temperature was allowed to rise. Thin layer chromatography showed an incomplete reaction. Another portion of methylhydrazine (3 ml) was added to the reaction mixture recooled to −78°. Reaction was essentially complete. The solvent was evaporated in vacuo overnight without heating to give 8.3 g (89%) of white solid. T.l.c. (5% $CH_3OH$ in $CHCl_3$) shows one major product (Rf≈0.4) plus several lower Rf minor products.

Anal. Calculated: C, 56.72; H, 5.57; N, 11.91 Found: C, 56.87; H, 5.64; N, 12.00

The material is the phthaloyl $N^1$-methylhydrazide (II, $R_1 = -CO_2CH_3$, $R_2 = DMB$).

A solution of 3.5 g of the half hydrazide in 50 ml of chloroform was heated on the steam bath at reflux for 30 minutes. A second portion was stirred at room temperature overnight with no heating: filtration and evaporation gave the free amino compound in both cases.

EXAMPLE 6

A solution of 2.6 g (0.0055 mole, prepared by reducing the 2-carbomethoxy compound with sodium borohydride and reacting the resulting 2-hydroxymethyl compound with methylsulfonyl chloride) of cis-3-phthalimido-1-(2,4-dimethoxybenzyl)-4-oxo-2-mesyloxymethylazetidine in 150 ml of methylene chloride was cooled under nitrogen in a dry ice-acetone bath with stirring. Methylhydrazine (98%, 0.25 g) was added at once. The reaction mixture was allowed to warm to room temperature overnight. The resulting IV by-product was separated and the organic solution was washed with 3 N hydrochloric acid (3 × 50 ml). The aqueous fraction was extracted with methylene chloride then neutralized to pH 8 with 10% sodium hydroxide solution. The organic matter was extracted with methylene chloride. The extracts were dried and evaporated to give a yellow oil of the desired aminomesyl compound (84%). T.l.c. on silica gel with 5% methanol/chloroform gave a major spot at Rf ∼ 0.3.

EXAMPLE 7

2,4-Dimethoxybenzylamine (5.01 g, 0.03 mol) and benzyl glyoxalate (0.036 mol) were condensed as in Example 1 at 0°–5° for 2 hours. The resulting imine was dissolved in methylene chloride (800 ml) and cooled in an ice bath. Triethylamine (5.4 ml) was added followed by the dropwise addition of a solution of N-phthalimidoacetic acid chloride (7.54 g, 0.0338 mol) [J. Amer. Chem. Soc., 71, 1856 (1949)] in methylene chloride (80 ml). After the reaction was stirred 2 hours, the solution concentrated and then washed with water, dilute hydrochloric acid, and dilute bicarbonate. The dried organic phase was evaporated to give benzyl cis-1-(2,4-dimethoxybenzyl)-3-phthalimido-4-oxoazetidine-2-carboxylate which can be optionally purified over silica gel in 10% ethyl acetate/chloroform.

The crude phthalimido product (1 g) in chloroform is reacted at −50° with an excess of methyl hydrazine to give the half or open hydrazide (II, $R_1 = -CO_2CH_2C_6H_5$, $R_2 = DMB$) which is allowed to stand at room temperature overnight to give the desired amino compound.

EXAMPLE 8

A mixture of 12.0 g (0.28 mol) of cis-3-phthalimido-4-carbomethoxy-1-(2,4-dimethoxybenzylazetidin-2-one in 900 ml of dry methylene chloride is cooled in a dry ice-acetone bath under nitrogen. To this solution 15 g. (0.36 mol) of methylhydrazide was added over a 5–10 minute period. The cooling bath was left in place and stirring was continued overnight as the temperature rose to room temperature. The insoluble IV by-product was separated by filtration and the mother solution extracted with 3N hydrochloric acid (<300 ml). The aqueous solution was then washed with methylene chloride, cooled and the pH taken to 7.5 with 10% sodium hydroxide. The resulting cloudy solution was extracted with methylene chloride and dried. Evaporation gave a pale yellow oil which when triturated with petroleum ether gives a white solid (70.5 g, 86%).

What is claimed is:

1. The compound of the formula:

in which:

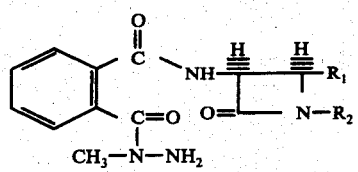

$R_1$ is —COOY or —CH$_2$OZ;

$R_2$ is 2,4-dimethoxybenzyl, hydrogen, benzhydryl, trityl,

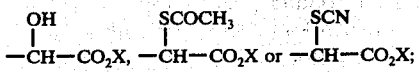

Y is lower alkyl of 1-6 carbons, benzyl, phenyl or 2,2,2-trichloroethyl;

Z is lower alkyl of 1-6 carbons, alkanoyl of 2-6 carbons, mesyl, tosyl or benzyl; and X is benzhydryl, 2,2,2-trichloroethyl or p-nitrophenyl.

2. The compound of claim 1 in which $R_1$ is —COOCH$_3$, and $R_2$ is 2,4-dimethoxybenzyl.

3. The compound of claim 1 in which $R_1$ is —COOCH$_3$ and $R_2$ is hydrogen.

4. The compound of claim 1 in which $R_1$ is —COOCH$_2$C$_6$H$_5$ and $R_2$ is 2,4-dimethoxybenzyl.

5. The compound of claim 1 in which $R_1$ is —CH$_2$O mesyl and $R_2$ is 2,4-dimethoxybenzyl.

* * * * *